United States Patent
Sitaraman et al.

(10) Patent No.: US 11,634,431 B2
(45) Date of Patent: Apr. 25, 2023

(54) PROCESS FOR PURIFICATION OF PROTECTED POLYCYCLIC CARBAMOYLPYRIDONE DERIVATIVES

(71) Applicant: LAURUS LABS LIMITED, Hyderabad (IN)

(72) Inventors: Srinivasan Sitaraman, Hyderabad (IN); Ravikanth Sribhashyam, Hyderabad (IN); Ravinder Paladi, Hyderabad (IN)

(73) Assignee: Laurus Labs Limited, Hyderabad (IN)

( * ) Notice: Subject to any disclaimer, the term of this patent is extended or adjusted under 35 U.S.C. 154(b) by 247 days.

(21) Appl. No.: 17/259,279

(22) PCT Filed: Jul. 11, 2019

(86) PCT No.: PCT/IB2019/055925
§ 371 (c)(1),
(2) Date: Jan. 11, 2021

(87) PCT Pub. No.: WO2020/012408
PCT Pub. Date: Jan. 16, 2020

(65) Prior Publication Data
US 2021/0269457 A1    Sep. 2, 2021

(30) Foreign Application Priority Data
Jul. 12, 2018  (IN) .............................. 201841026007

(51) Int. Cl.
*C07D 498/14* (2006.01)
*C07D 498/18* (2006.01)

(52) U.S. Cl.
CPC ......... *C07D 498/14* (2013.01); *C07D 498/18* (2013.01)

(58) Field of Classification Search
CPC ........................... C07D 498/14; C07D 498/18
See application file for complete search history.

(56) References Cited

U.S. PATENT DOCUMENTS

| | | |
|---|---|---|
| 8,129,385 B2 | 3/2012 | Johns et al. |
| 8,552,187 B2 | 10/2013 | Johns et al. |
| 8,889,877 B2 | 11/2014 | Goodman et al. |
| 9,216,996 B2 | 12/2015 | Jin et al. |
| 2014/0011995 A1 | 1/2014 | Sumino et al. |
| 2016/0108058 A1 | 4/2016 | Budidet et al. |

FOREIGN PATENT DOCUMENTS

| | | |
|---|---|---|
| IN | 247/CHE/2014 | 8/2015 |
| IN | 1006/MUM/2015 | 9/2016 |
| IN | 1007/MUM/201 | 9/2016 |
| WO | WO 2014/100323 A1 | 6/2014 |
| WO | WO 2015/019310 A1 | 2/2015 |
| WO | WO 2015/177537 A1 | 11/2015 |
| WO | WO 2015/195656 A2 | 12/2015 |
| WO | WO 2016/092527 A1 | 6/2016 |
| WO | WO 2016/113372 A1 | 7/2016 |
| WO | WO 2016/125192 A2 | 8/2016 |

OTHER PUBLICATIONS

Johns; J. Med. Chem. 2013, 56, 14, 5901-5916. https://doi.org/10.1021/jm400645w (Year: 2013).*
Sankareswaran; Org. Process Res. Dev. 2016, 20, 8, 1461-1468. https://doi.org/10.1021/acs.oprd.6b00156 (Year: 2016).*

* cited by examiner

*Primary Examiner* — Daniel R Carcanague
(74) *Attorney, Agent, or Firm* — Blank Rome LLP

(57) ABSTRACT

The present invention relates to a process for purification of protected polycyclic carbamoylpyridone derivatives and its conversion to polycyclic carbamoylpyridone derivatives or its pharmaceutically acceptable salts thereof.

17 Claims, 4 Drawing Sheets

Where P is hydroxy protecting group; M is alkali metal ion; R is variant derived from cyclic anhydride

PROCESS FOR PURIFICATION OF PROTECTED POLYCYCLIC CARBAMOYLPYRIDONE DERIVATIVES

CROSS-REFERENCE TO RELATED APPLICATIONS

This is a national phase application that is based on and claims the benefit of International Application No. PCT/IB2019/055925, filed on Jul. 11, 2019, which is based on and claims the benefit of the filing date and disclosure of Indian Provisional Application No. 201841026007, filed on Jul. 12, 2018, the contents of which are incorporated by reference herein.

FIELD OF THE INVENTION

The present invention relates to a process for purification of protected polycyclic carbamoylpyridone derivatives and its conversion to polycyclic carbamoylpyridone derivatives or its pharmaceutically acceptable salts thereof.

BACKGROUND OF THE INVENTION

Polycyclic carbamoylpyridone derivatives are known to act as a Human Immunodeficiency Virus type-I (HIV-I) integrase strand transfer inhibitors in combination with other antiretroviral medicinal products for the treatment of HIV-1 infection.

U.S. Pat. Nos. 8,129,385 and 9,216,996 disclose various polycyclic carbamoylpyridone derivatives and process for their preparation, which are incorporated herein in their entirety by reference. Among those polycyclic compounds, the tricyclic carbamoyl pyridone derivatives represented by the following structural Formula I found to have superior potency against resistant viral strains;

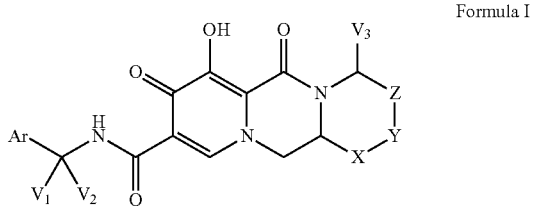

Formula I or a stereoisomer or pharmaceutically acceptable salt thereof; wherein Ar is aryl substituted with one to three halogens;

$V_1$ and $V_2$ are each independently, hydrogen, $C_{1-6}$ alkyl, or $C_{1-6}$ haloalkyl; or $V_1$ and $V_2$ together with the carbon atom to which they are attached, form a carbocyclic ring having from 3 to 6 ring atoms or a heterocyclic ring having from 3 to 6 ring atoms, wherein the carbocyclic or a heterocyclic ring is optionally substituted with one or more $R^a$ group;

X is —O— or —$NV_4$— or —$CHV_4$;

Y is —$CHV_5$;

Z is a bond, (—$CH_2$—)$_n$ or Y and Z taken together form (—$CH_2$—)$_n$; wherein n is an integer of 0 to 3.

$V_3$, $V_4$ and $V_5$ are each independently, hydrogen or $C_{1-6}$ alkyl, $C_{6-14}$ aryl or Wherein $V_3$ and $V_4$ or $V_3$ and $V_5$ taken together form a carbocyclic ring containing having from 3 to 6 ring atoms or a heterocyclic ring having from 3 to 6 ring atoms, wherein the carbocyclic or heterocyclic ring is optionally substituted with one or more $R^a$ group, wherein each $R^a$ is, independently, hydrogen, halo, hydroxyl or $C_{1-6}$ alkyl, or wherein two $R^a$ groups together with the carbon atom to which they are attached to form =O;

Preferred tricyclic carbamoyl pyridone derivatives of Formula I includes but not limited to the following compounds of Formula IA, Formula IB and Formula IC;

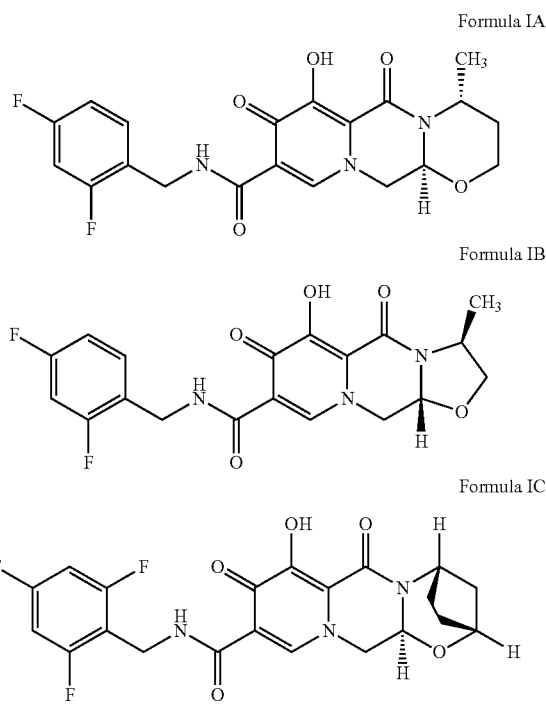

Formula IA is commonly known as dolutegravir which is approved by FDA under the brand name of TIVICAY by ViiV Healthcare and manufactured by GlaxoSmithKline.

Formula IB is commonly known as cabotegravir. Cabotegravir is an investigational integrase strand transfer inhibitor (INSTI) being developed by ViiV Healthcare for the treatment and prevention of HIV and currently under phase III clinical trials.

Formula IC is commonly known as bictegravir. Bictegravir in combination with emtricitabine/tenofovir alafenamide as a fixed dose combination drug was approved in United States by FDA for the treatment of HIV-1 infection.

Protected tricyclic carbamoylpyridone derivatives represented by following structural Formula II is one of the important intermediate in the preparation of tricyclic carbamoylpyridone derivatives of Formula (I)

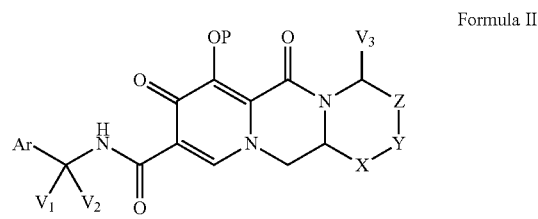

Formula II or a stereoisomer thereof; wherein P is a hydroxy protecting group; Ar, $V_1$, $V_2$, $V_3$, X, Y and Z are as defined above for Formula I.

Preparation of protected tricyclic carbamoylpyridone derivatives of Formula II and its conversion to polycyclic carbamoylpyridone derivatives of Formula I were disclosed in different patents and publications; for example, U.S. Pat. Nos. 8,129,385, 9,216,996, 8,552,187, U.S. Pat. No. 8,889, 877, US20140011995, US20160108058, WO2015019310, WO2015195656, WO2015177537, WO2016092527, WO2016113372, WO2016125192, 1006/MUM/2015 and 1007/MUM/201 and 247/CHE/2014. When the present inventors carried out the preparation of Formula II using the reported process, found that open chain impurity having structural Formula III has been formed in substantial amount along with Formula II.

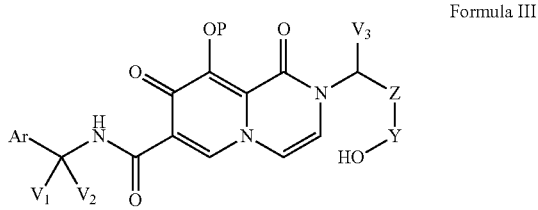

Formula III wherein P, Ar, $V_1$, $V_2$, $V_3$, Y and Z are as defined above for Formula II.

An article published in Organic Process Research and Development, 20, 1461-1468, 2016, discloses optimized process for the preparation of dolutegravir along with origin of impurities and process to control the same. The said journal also describes the formation of open chain impurity having the following structural formula

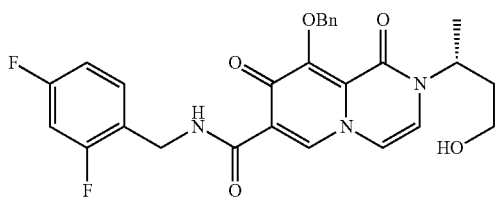 [SMILES: C[C@H](CCO)n1ccn2cc(C(=O)NCc3ccc(F)cc3F)c(=O)c(OCc3ccccc3)c2c1=O]

along with benzyl protected dolutegravir in substantial amount. The same impurity was identified as a critical impurity by author, as it reacted in subsequent stages and carried forward to final stages and was not purged by regular purification process in final stage. Further states that, this open chain impurity is formed by competitive dealkylation of the ether moiety in a ring under acidic conditions, which cannot be controlled or removed by regular process parameters such as modification trials or other purification technique.

The said journal also described a process for removal of open chain impurity from benzyl protected dolutegravir by selective derivatization with TBDMS-Cl in presence of imidazole in methylene chloride, followed by isolating pure benzyl protected dolutegravir by crystallization from methanol after workup process. However, the described process involves use of costly TBDMS-Cl reagent for derivatization and additional crystallization at reflux temperature required to separate pure benzyl protected dolutegravir from impurity, which prolong production time and increases cost of production. The said process is time consuming, expensive, not cost competitive and thus, not very suitable on commercial scale.

Thus, the main objective of the present invention is to provide an economical process for purification of protected tricyclic carbamoylpyridone derivative of Formula II, which avoids costly reagents and separate crystallization step to remove open chain impurity.

SUMMARY OF THE INVENTION

Accordingly, the present invention provides a process for purification of protected tricyclic carbamoylpyridone derivatives of Formula II or a stereoisomer thereof, and its conversion to tricyclic carbamoylpyridone derivatives of Formula I or a stereoisomer or pharmaceutically acceptable salt thereof.

In one aspect, the present invention provides a process for purification of protected tricyclic carbamoylpyridone derivatives of Formula II,

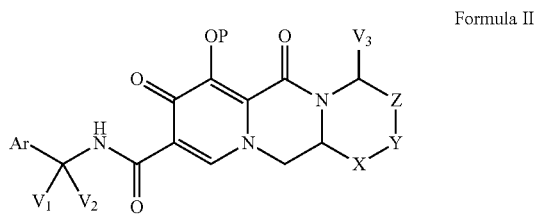

Formula II or a stereoisomer thereof; wherein

P is hydroxy protecting group selected from straight or branched chain $C_{1-8}$ alkyl group, $C_{1-8}$ halo alkyl, substituted or unsubstituted silyl or $C_{6-14}$ aryl;

Ar is aryl substituted with one to three halogens;

$V_1$ and $V_2$ are each independently, hydrogen, $C_{1-6}$ alkyl, or $C_{1-6}$ haloalkyl; or $V_1$ and $V_2$ together with the carbon atom to which they are attached, form a carbocyclic ring having from 3 to 6 ring atoms or a heterocyclic ring having from 3 to 6 ring atoms, wherein the carbocyclic or a heterocyclic ring is optionally substituted with one or more $R^a$ group;

X is —O—;

Y is —$CHV_5$;

Z is a bond, $(—CH_2—)_n$ or Y and Z taken together form $(—CH_2—)_n$; wherein n is an integer of 0 to 3;

$V_3$ and $V_5$ are each independently, hydrogen or $C_{1-6}$ alkyl, $C_{6-14}$ aryl; or wherein $V_3$ and $V_5$ taken together form a carbocyclic ring containing having from 3 to 6 ring atoms or a heterocyclic ring having from 3 to 6 ring atoms, wherein the carbocyclic or heterocyclic ring is optionally substituted with one or more $R^a$ group, wherein each $R^a$ is, independently, hydrogen, halo, hydroxyl or $C_{1-6}$ alkyl, or wherein two $R^a$ groups together with the carbon atom to which they are attached to form =O;

which comprises;

a) reacting a compound of Formula II comprising a compound of Formula III,

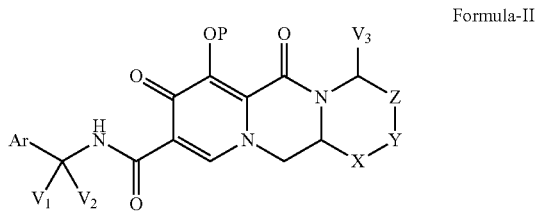

Formula-II

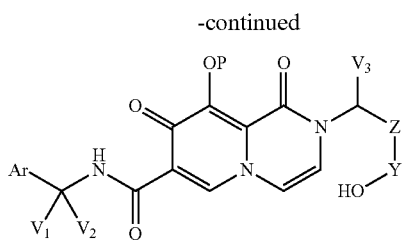

Formula III wherein P, Ar, $V_1$, $V_2$, $V_3$, X, Y and Z are as defined above; with a $C_2$-$C_{20}$ substituted or unsubstituted cyclic anhydride in a suitable solvent; and b) isolating the compound of Formula II substantially free of compound of Formula III.

In another aspect, the present invention provides a process for purification of protected tricyclic carbamoylpyridone derivatives of Formula II, which comprises;

a) reacting a compound of Formula II comprising a compound of Formula III, wherein P, Ar, $V_1$, $V_2$, $V_3$, X, Y and Z are as defined above, with a $C_2$-$C_{20}$ substituted or unsubstituted cyclic anhydride in a suitable solvent;

b) treating the reaction mass with an aqueous basic solution; and c) isolating the compound of Formula II substantially free of compound of Formula III.

In another aspect, the present invention provides a process for purification of protected tricyclic carbamoylpyridone derivatives of Formula II, which comprises;

a) reacting a compound of Formula II comprising a compound of Formula III, wherein P, Ar, $V_1$, $V_2$, $V_3$, X, Y and Z are as defined above, with a $C_2$-$C_{20}$ substituted or unsubstituted cyclic anhydride in a suitable solvent;

b) treating the reaction mass with an aqueous basic solution;

c) separating the organic layer and aqueous layer;

d) concentrating the organic layer; and e) isolating the compound of Formula II substantially free of compound of Formula III.

In another aspect, the present invention provides a process for preparation of tricyclic carbamoylpyridone derivatives of Formula I,

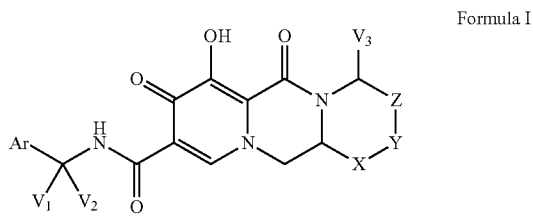

Formula I or a stereoisomer or pharmaceutically acceptable salt thereof; wherein Ar is aryl substituted with one to three halogens;

$V_1$ and $V_2$ are each independently, hydrogen, $C_{1-6}$ alkyl, or $C_{1-6}$ haloalkyl; or $V_1$ and $V_2$ together with the carbon atom to which they are attached, form a carbocyclic ring having from 3 to 6 ring atoms or a heterocyclic ring having from 3 to 6 ring atoms, wherein the carbocyclic or a heterocyclic ring is optionally substituted with one or more $R^a$ group;

X is —O—;

Y is —$CHV_5$;

Z is a bond, (—$CH_2$—)$_n$ or Y and Z taken together form (—$CH_2$—)$_n$; wherein n is an integer of 0 to 3;

$V_3$ and $V_5$ are each independently, hydrogen or $C_{1-6}$ alkyl, $C_{6-14}$ aryl or wherein $V_3$ and $V_5$ taken together form a carbocyclic ring containing having from 3 to 6 ring atoms or a heterocyclic ring having from 3 to 6 ring atoms, wherein the carbocyclic or heterocyclic ring is optionally substituted with one or more $R^a$ group;

wherein each $R^a$ is, independently, hydrogen, halo, hydroxyl or $C_{1-6}$ alkyl, or wherein two $R^a$ groups together with the carbon atom to which they are attached to form =O; which comprises;

i) reacting a compound of Formula II or a stereoisomer thereof comprising a compound of Formula III or a stereoisomer thereof, wherein P, Ar, $V_1$, $V_2$, $V_3$, X, Y and Z are as defined above, with a $C_2$-$C_{20}$ substituted or unsubstituted cyclic anhydride or mixtures thereof in a suitable solvent;

ii) treating the reaction mass with aqueous basic solution;

iii) isolating the compound of Formula II substantially free of compound of Formula III; and iv) converting the compound of Formula II in to compound of Formula I by hydroxy group deprotection.

In another aspect, the present invention provides a process for purification of methoxy derivative compound of Formula IIA, which comprises;

a) reacting a compound of Formula IIA comprising a compound of Formula IIIA

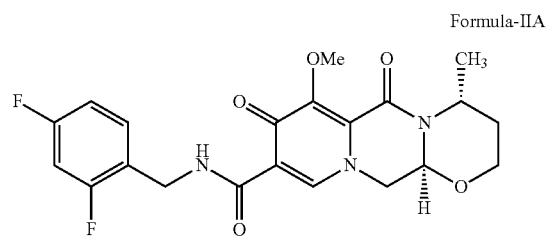

Formula-IIA

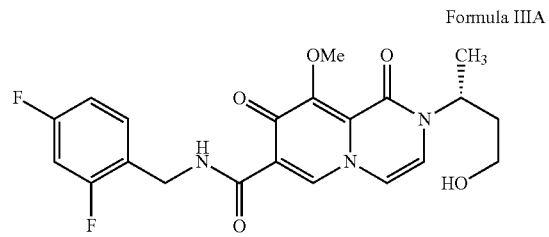

Formula IIIA with a $C_2$-$C_{20}$ substituted or unsubstituted cyclic anhydride in a suitable solvent in presence of a base;

b) treating the reaction mass with an aqueous basic solution;

c) separating the organic layer and aqueous layer;

d) concentrating the organic layer, and e) isolating the compound of Formula IIA substantially free of compound of Formula IIIA.

In another aspect, the present invention provides a process for purification of methoxy derivative compound of Formula IIB, which comprises;
a) reacting a compound of Formula IIB comprising a compound of Formula IIIB

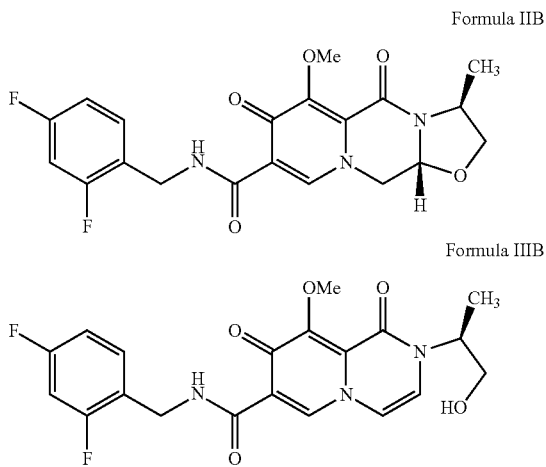

with a $C_2$-$C_{20}$ substituted or unsubstituted cyclic anhydride in a suitable solvent in presence of a base;
b) treating the reaction mass with an aqueous basic solution;
c) separating the organic layer and aqueous layer;
d) concentrating the organic layer, and
e) isolating the compound of Formula IIB substantially free of compound of Formula IIIB.

In another aspect, the present invention provides a process for purification of methoxy derivative compound of Formula IIC, which comprises;
a) reacting a compound of Formula IIC comprising a compound of Formula IIIC

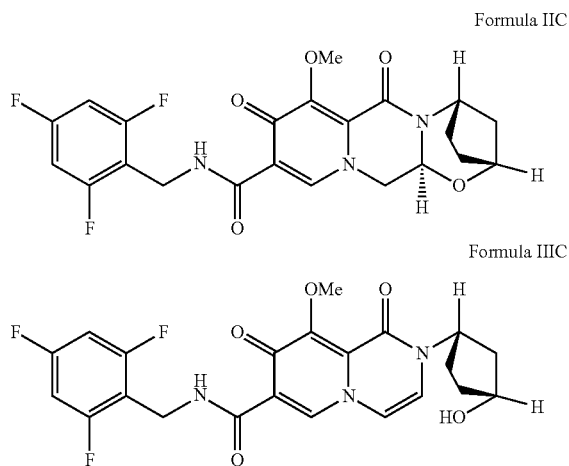

with a $C_2$-$C_{20}$ substituted or unsubstituted cyclic anhydride in a suitable solvent in presence of a base;
b) treating the reaction mass with an aqueous basic solution;
c) separating the organic layer and aqueous layer;
d) concentrating the organic layer, and
e) isolating the compound of Formula IIC substantially free of compound of Formula IIIC.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
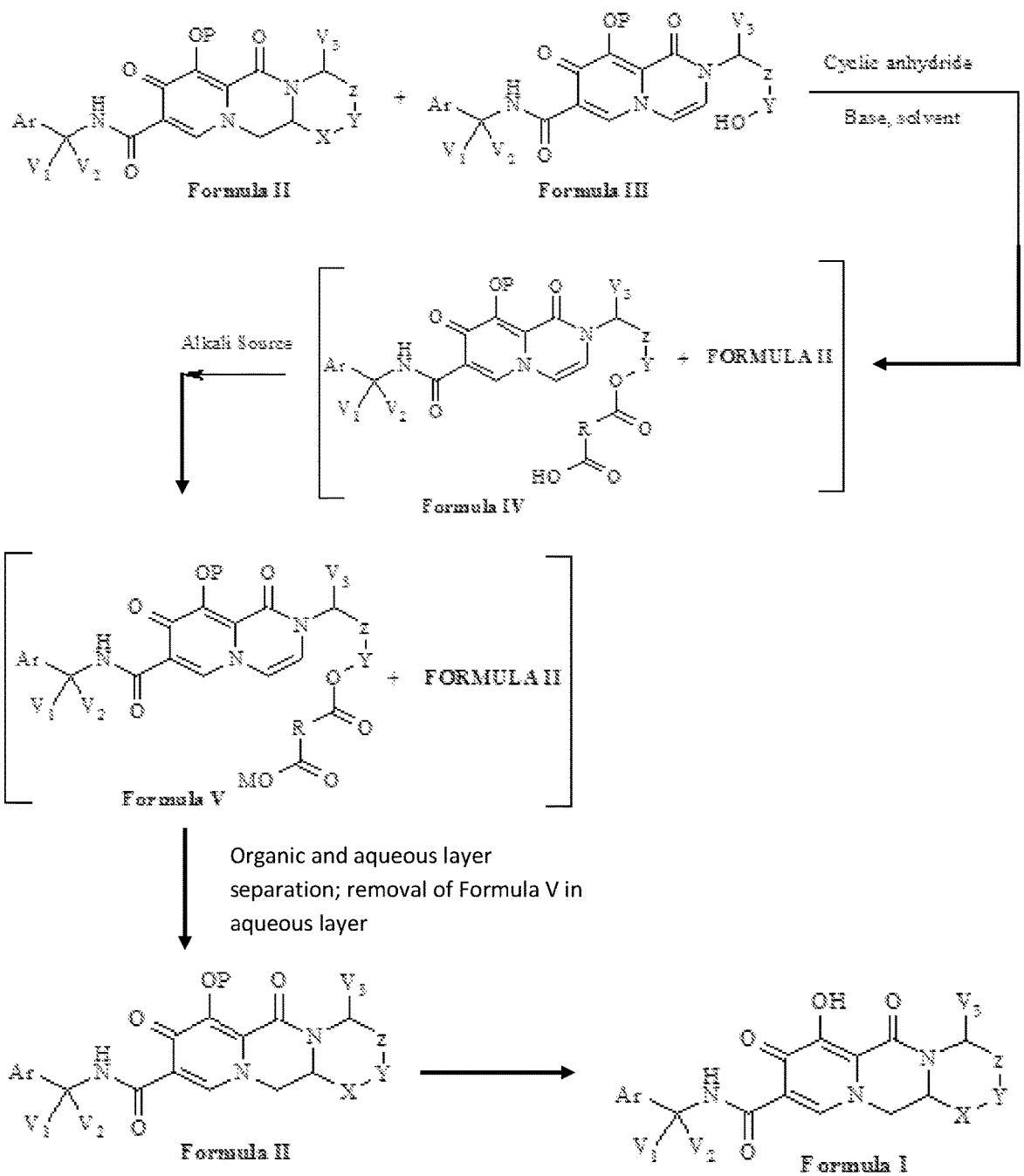
FIG. 1 shows schematic representation of process for the preparation of compound of Formula I of the present invention.
Figure 2:
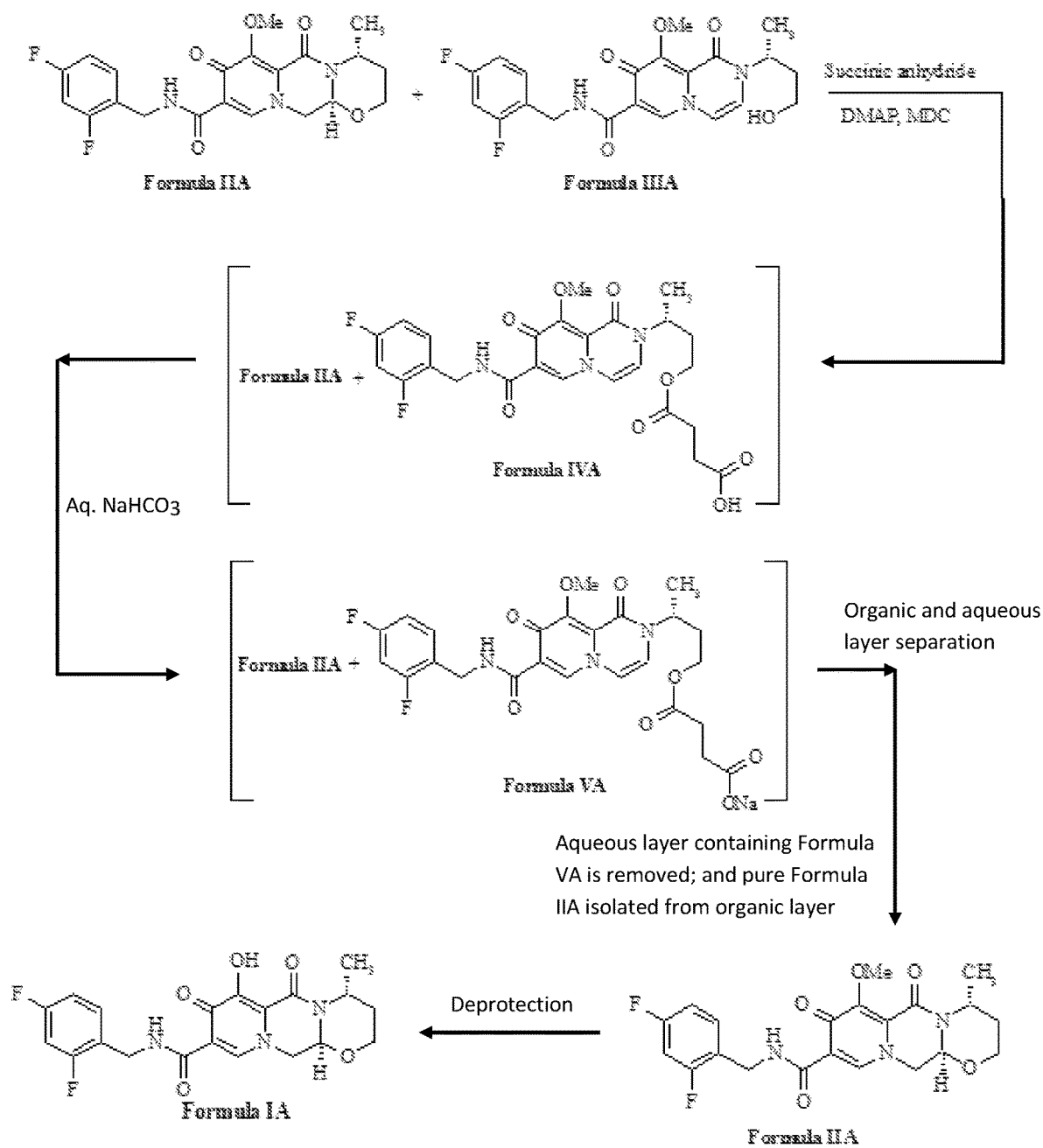
FIG. 2 shows schematic representation of process for the preparation of compound of Formula IA of the present invention.
Figure 3:
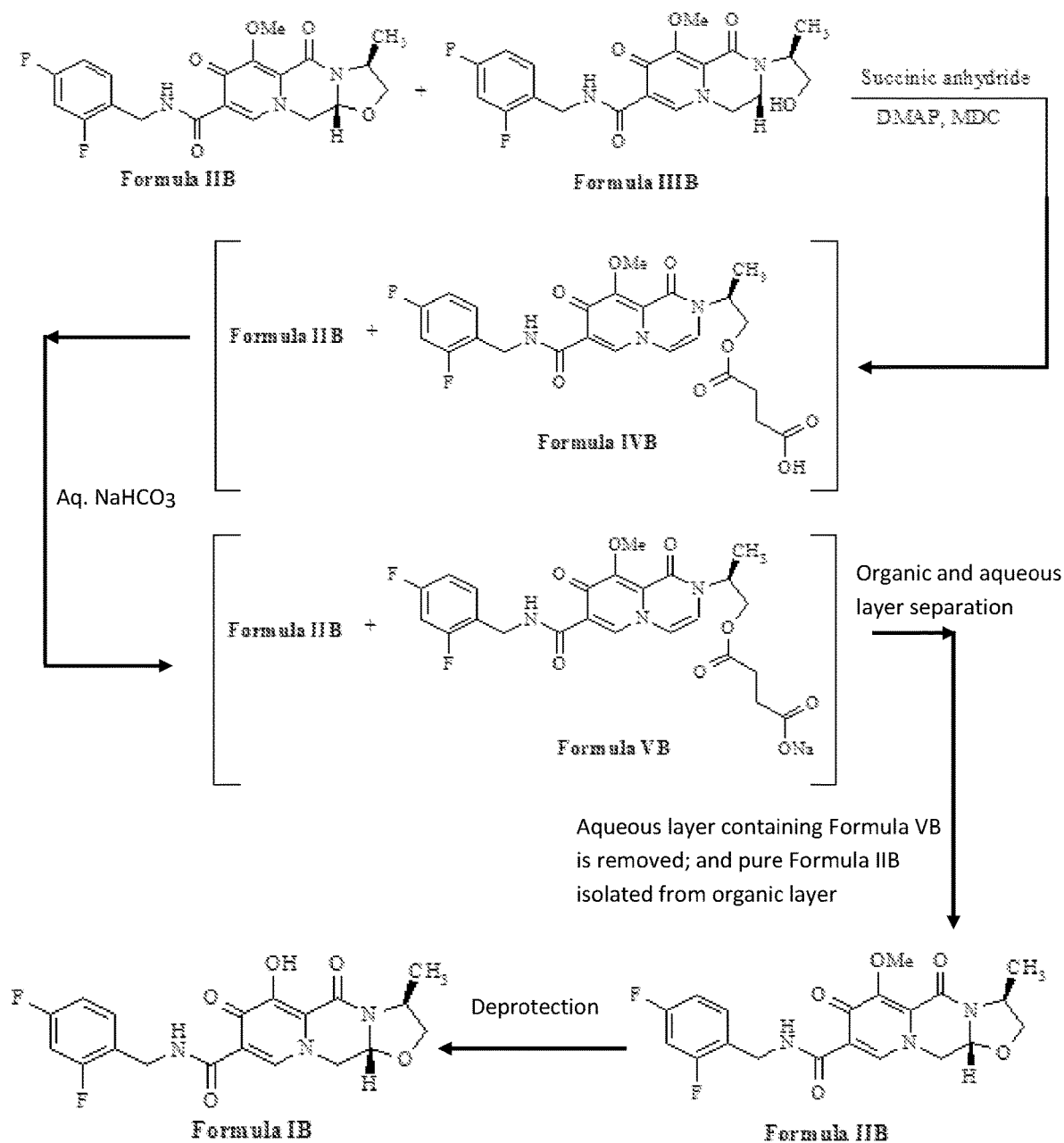
FIG. 3 shows schematic representation of process for the preparation of compound of Formula IB of the present invention.
Figure 4:
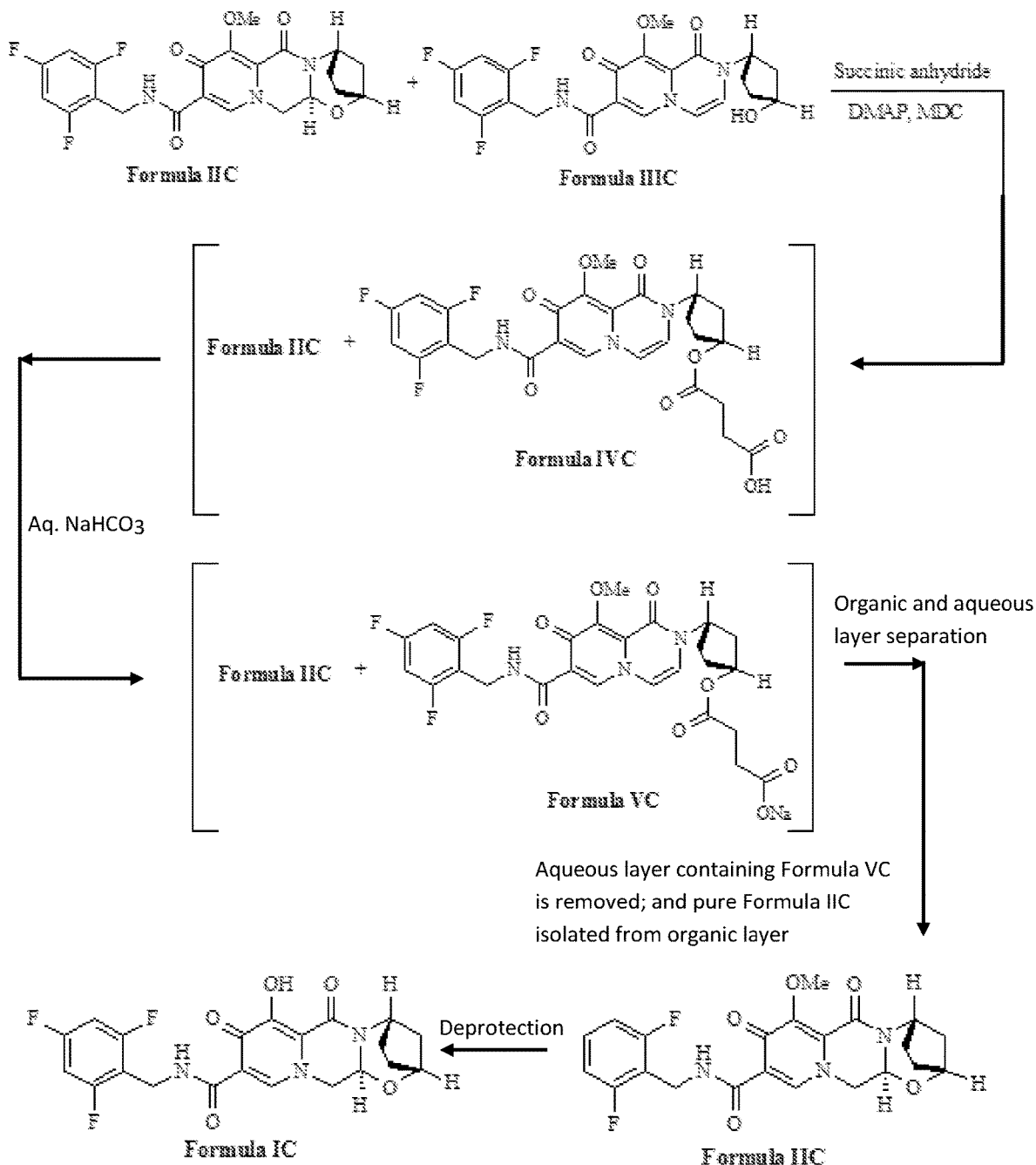
FIG. 4 shows schematic representation of process for the preparation of compound of Formula IC of the present invention.

Unless otherwise specified the term "alkyl" used herein the specification represents $C_1$ to $C_6$ or $C_1$ to $C_8$ alkyl and is selected from but not limited to, methyl, ethyl, propyl, isopropyl, butyl, isobutyl, pentyl, hexyl, isoamyl and the like.

Unless otherwise specified the term "aryl" used herein the specification represents $C_{6-14}$ aryl and is selected from but not limited to, phenyl, napthyl and the like.

Unless otherwise specified the term "halo alkyl" used herein the specification represents an alkyl radical substituted by one or more halo radicals, and is selected from but not limited to, trifluoromethyl, difluoromethyl, trichloromethyl, 2,2,2-trifluoroethyl, 1,2-difluoroethyl, 3-bromo-2-fluoropropyl and the like.

Unless otherwise specified the term "carbocyclic ring" used herein the specification represents carbocyclic ring having three to six carbon atoms and is selected from but not limited to cyclopropyl, cyclobutyl, cyclopentyl and the like.

Unless otherwise specified the term "heterocyclic ring" used herein the specification represents heterocyclic ring having three to six carbon atoms and contains at least one hetero atoms selected from nitrogen, oxygen and sulfur, and is selected from but not limited to dioxolanyl, oxazolidinyl, piperidinyl, tetrahydrofuryl, imidazolinyl and the like.

Unless otherwise specified the term "aralkyl" used herein the specification refers to an alkyl group substituted by an aryl group and is selected from but not limited to, benzyl, phenylethyl and the like.

Unless otherwise specified the term "substituted or unsubstituted silyl" used herein the specification refers to trialkylsilyl, triaryl silyl or trialkylarylsilyl group and are selected from but not limited to, trimethylsilyl, triethylsilyl, t-butyldimethylsilyl, t-butyldiphenylsilyl triphenylsilyl and the like.

Unless otherwise specified the term "halogen" or "halo" used herein the specification refers to bromo, chloro, fluoro or iodo.

The present invention provides a process for purification of protected tricyclic carbamoylpyridone derivatives of Formula II or a stereoisomer thereof and its conversion to tricyclic carbamoylpyridone derivatives of Formula I or a stereoisomer or pharmaceutically acceptable salt thereof.

In one embodiment, the present invention provides a process for purification of protected tricyclic carbamoylpyridone derivatives of Formula II,

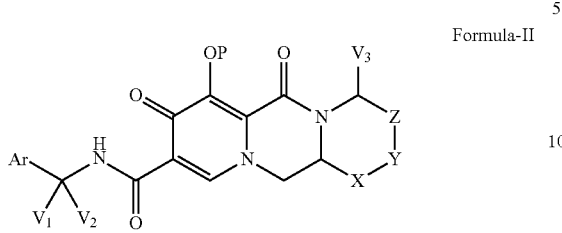

Formula-II or a stereoisomer thereof; wherein

P is hydroxy protecting group selected from straight or branched chain $C_{1-8}$ alkyl group;

$C_{1-8}$ halo alkyl, substituted or unsubstituted silyl, $C_{6-14}$ aryl or aralkyl;

Ar is aryl substituted with one to three halogens;

$V_1$ and $V_2$ are each independently, hydrogen, $C_{1-6}$ alkyl, or $C_{1-6}$ haloalkyl; or $V_1$ and $V_2$ together with the carbon atom to which they are attached, form a carbocyclic ring having from 3 to 6 ring atoms or a heterocyclic ring having from 3 to 6 ring atoms, wherein the carbocyclic or a heterocyclic ring is optionally substituted with one or more $R^a$ group;

X is —O—;

Y is —CHV$_5$;

Z is a bond, (—CH$_2$—)$_n$ or Y and Z taken together form (—CH$_2$—)$_n$; wherein n is an integer of 0 to 3;

$V_3$ and $V_5$ are each independently, hydrogen or $C_{1-6}$ alkyl, $C_{6-14}$ aryl or Wherein $V_3$ and $V_5$ taken together form a carbocyclic ring containing having from 3 to 6 ring atoms or a heterocyclic ring having from 3 to 6 ring atoms, wherein the carbocyclic or heterocyclic ring is optionally substituted with one or more $R^a$ group, wherein each $R^a$ is, independently, hydrogen, halo, hydroxyl or $C_{1-6}$ alkyl, or wherein two $R^a$ groups together with the carbon atom to which they are attached to form =O;

which comprises;

a) reacting a compound of Formula II comprising a compound of Formula III,

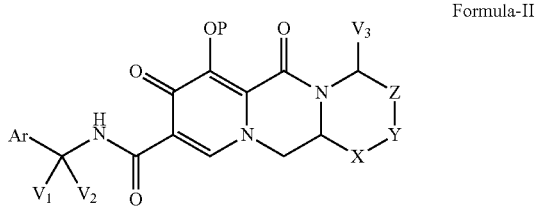

Formula-II

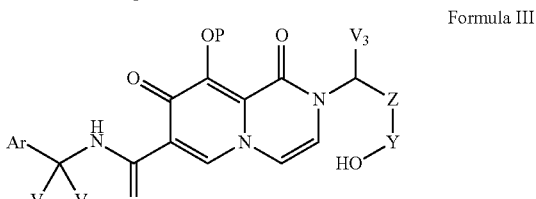

Formula III wherein P, Ar, $V_1$, $V_2$, $V_3$, X, Y and Z are as defined above; with $C_2$-$C_{20}$ substituted or unsubstituted cyclic anhydride or mixtures thereof in a suitable solvent;

b) treating the reaction mass with aqueous basic solution; and c) isolating the compound of Formula II substantially free of compound of Formula III.

The protected tricyclic carbamoylpyridone derivative compound of Formula II or a stereoisomer thereof, which is used herein as a starting material is known in the art and can be prepared by any known methods. For example, may be prepared as per the process disclosed in U.S. Pat. No. 8,889,877 or U.S. Pat. No. 9,216,996.

The starting compound of Formula II or a stereoisomer thereof may contains about 0.1% to about 5% of the compound of Formula III or a stereoisomer thereof, as an impurity as measured by HPLC. Further the said compound of Formula II may be obtained directly from the reaction mass in the form of crude, or a solution comprising mixture of compound of Formula II and Formula III or may be in the form of semi-solid or solid.

The step a) of the forgoing process involves reacting the compound of Formula II comprising a compound of Formula III, with $C_2$-$C_{20}$ substituted or unsubstituted cyclic anhydride and mixtures thereof, wherein the substituents may be selected from $C_1$-$C_{20}$ alkyl, alkenyl, ether, thioether, alkylhalide, or halide; More preferably the $C_2$-$C_{20}$ substituted or unsubstituted cyclic anhydride is selected from succinic anhydride, phthalic anhydride, glutaric anhydride or maleic anhydride; most preferably succinic anhydride; wherein P, Ar, $V_1$, $V_2$, $V_3$, Y and Z are as defined above; more preferably P is methyl; Ar is 2,4-difluorophenyl or 2,4,6-trifluorophenyl; X is —O; Y is CHV$_5$, Z is —CH$_2$ or Y and Z taken together form a (—CH$_2$—)$_n$, wherein n is 1. $V_1$, $V_2$ and $V_5$ are independently hydrogen; $V_3$ is methyl or $V_3$ and $V_5$ together form cyclopentane ring.

In an embodiment, the compound of Formula II and compound of Formula III are specifically represented as following compound of Formula IIA and Formula IIIA respectively;

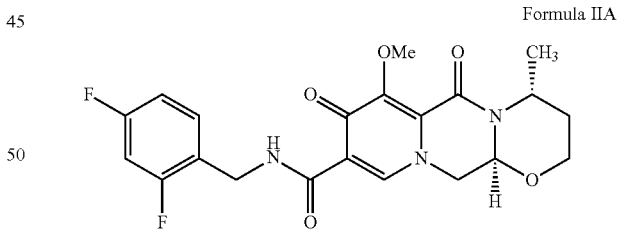

Formula IIA

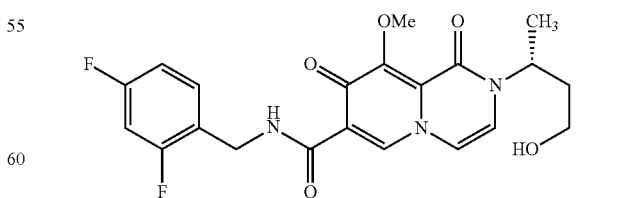

Formula IIIA

In an embodiment, the compound of Formula II and compound of Formula III are specifically represented as the following compound of Formula IIB and Formula IIIB respectively;

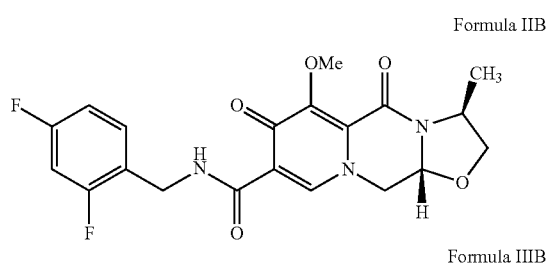

Formula IIB

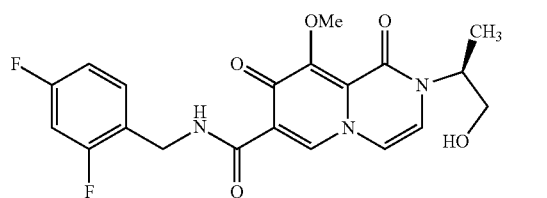

Formula IIIB

In an embodiment, the compound of Formula II and compound of Formula III are specifically represented as the following compound of Formula IIC and Formula IIIC respectively;

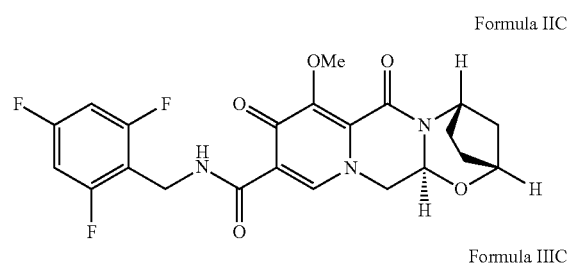

Formula IIC

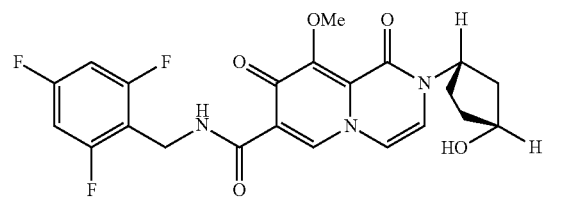

Formula IIIC

The suitable solvent used herein step a) is selected from the group consisting of but not limited to halogenated hydrocarbons, such as methylene chloride, chloroform, or chlorobenzene; hydrocarbons, such as toluene, xylene, heptane, or hexane; ketones, such as such as acetone, methyl ethyl ketone, methyl isobutyl ketone, or diethyl ketone; esters, such as ethyl acetate, propyl acetate, isopropyl acetate, or butyl acetate; ethers, such as tetrahydrofuran, dimethyl ether, isopropyl ether, methyl tertiary butyl ether or 1,4-dioxane; nitriles, such as acetonitrile or propionitrile; amides, such as formamide, N,N-dimethylformamide or N,N-dimethylacetamide; sulfoxides, such as dimethylsulfoxide; and mixtures thereof; preferably the solvent is halogenated hydrocarbons and more preferably methylene chloride.

The step a) reaction may suitably be carried out in presence of a base, wherein the base is selected from the group consisting of triethylamine, isopropyl ethylamine, diisopropyl amine, diisopropyl ethylamine, N-methyl morpholine, 4-dimethylaminopyridine, piperidine, pyridine and the like and mixtures thereof; preferably 4-dimethylaminopyridine.

The step a) reaction may advantageously carried out at a suitable temperature of about 10° C. to about reflux temperature of the solvent used, preferably at a temperature of about 20-40° C., for a suitable period of time sufficient to form half ester-acid derivative represented by the following structural Formula IV with cyclic anhydride, preferably for about 2 to 6 hrs.

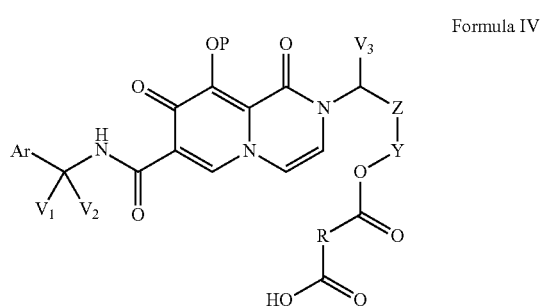

Formula IV wherein R is a variant derived from the corresponding cyclic anhydride utilized; P, Ar, $V_1$, $V_2$, $V_3$, Y, Z and Y are as defined above for formula I.

In an embodiment, the compound of Formula IV is specifically represented as the following compounds of Formula IVA, Formula IVA', Formula IVB, Formula IVB', Formula IVC or Formula IVC';

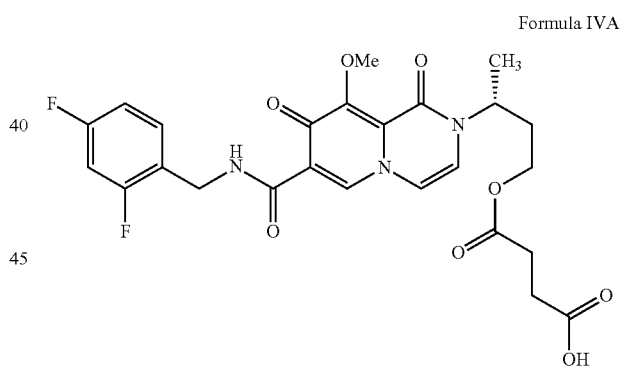

Formula IVA

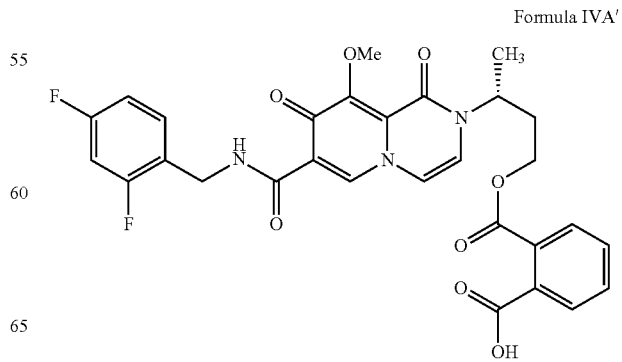

Formula IVA' bonates such as sodium bicarbonate, potassium bicarbonate and the like; preferably the base is alkali metal carbonates and more preferably sodium bicarbonate.

The treatment of step a) reaction mass with aqueous basic solution in step b) facilitates the removal of open chain impurity of Formula III by forming corresponding water soluble alkali salt of half ester-acid derivative represented by the following structural Formula V; and leaving the compound of Formula II substantially free of open chain impurity compound of Formula III in organic layer.

wherein M is alkali metal ion selected from Na, K, Cs and the like; P, Ar, $V_1$, $V_2$, $V_3$, Y, Z and R are as defined above.

In an embodiment, the compound of Formula V is specifically represented as the following compounds of Formula VA, Formula VA', Formula VB, Formula VB', Formula VC or Formula VC';

The step b) of the forgoing process involves treating the step a) reaction mass with aqueous basic solution; the aqueous basic solution is obtained by dissolving a suitable base in water, wherein the suitable base is selected from alkali metal carbonates such as sodium carbonate, potassium carbonate, cesium carbonate and the like; alkali metal bicar- -continued

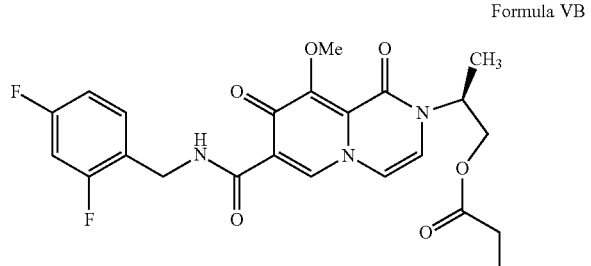
Formula VB

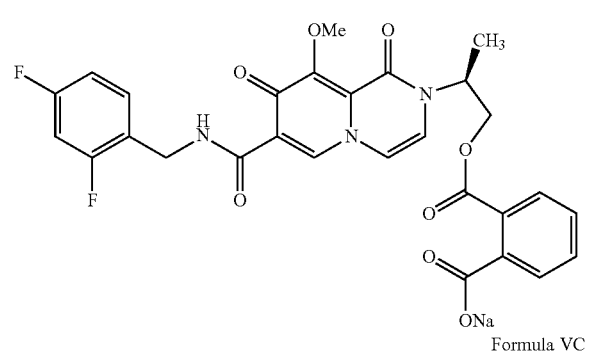
Formula VB'

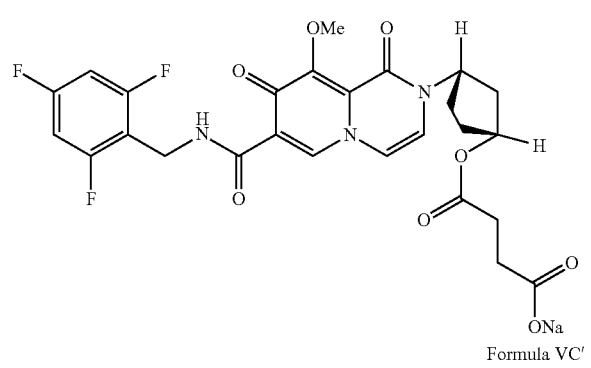
Formula VC

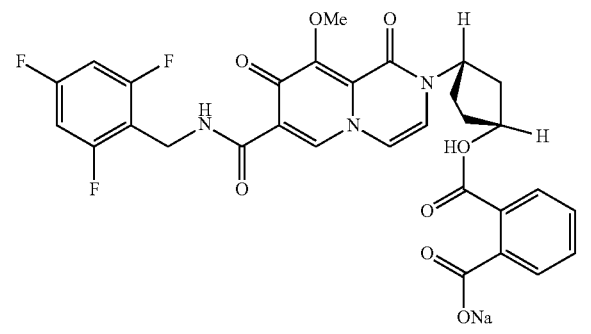
Formula VC'

The step b) reaction may advantageously carried out at a suitable temperature of about 15° C. to 40° C., preferably at a temperature of about 25-35° C., for a suitable period of time, preferably for about 30 mins.

After the step b) reaction, the organic layer containing compound of Formula II substantially free of open chain impurity compound of Formula III and aqueous layer containing alkali salt of half ester-acid derivative compound of formula V are separated by layer separation.

Then isolation of compound of Formula II substantially free of open chain impurity compound of Formula III from organic layer is carried out by the isolation methods known in the art. For example, concentrating the organic layer, adding suitable solvent followed by filtration. Preferably, concentrating the organic layer under vacuum, adding isopropyl ether to the obtained residue and stirring the reaction mass followed by filtration.

In another embodiment, the present invention provides a process for tricyclic carbamoylpyridone derivative of Formula I, which comprises;
  i) preparing protected tricyclic carbamoylpyridone derivative of Formula II or a stereoisomer thereof substantially free of open chain impurity compound of Formula III or a stereoisomer thereof; and
  ii) converting the compound of Formula II in to compound of formula I by hydroxy group deprotection.

The step i) of the forgoing process involves the preparation of compound of Formula II substantially free of compound of Formula III and can be prepared as per the present invention described in the previous embodiments.

The step ii) of forgoing process involves conversion of compound of Formula II to compound of Formula I by hydroxy group deprotection which can be carried out by the methods known in the art. For example, when P is alkyl, the deprotection step is suitably carried out by reaction with a Lewis acid selected from magnesium chloride, magnesium iodide, lithium chloride, lithium bromide, boron tribromide and the like; When P is aryl, the deprotection step is suitably carried out by hydrogenation in presence of catalyst selected from Pd/C, Pt/C, Raney-Ni and the like; When P is silyl, the deprotection step is suitably carried out by reaction with tetramethyl ammonium fluoride, tert-butyldimethylsilylether and the like. Further the deprotection step carried out in presence of a suitable solvent and at a suitable temperature from about 20° C. to reflux temperature of the solvent used.

In an embodiment, the compound of Formula I is specifically represented as the following compound of Formula IA or Formula IB or Formula IC;

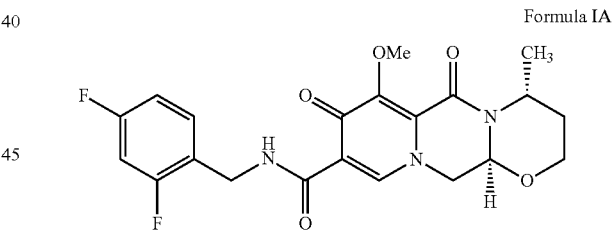
Formula IA

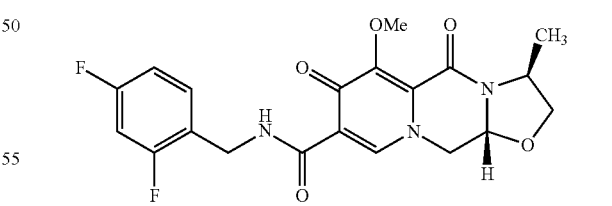
Formula IB

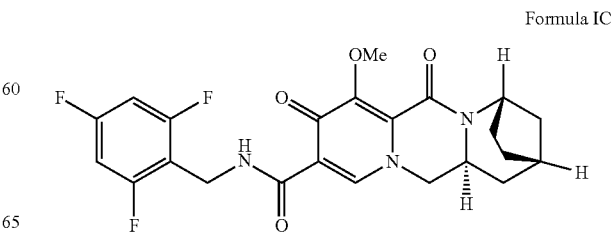
Formula IC

As used herein, the term "compound of Formula II substantially free of compound of Formula III", refers to a compound of Formula II containing less than about 0.1% of the compound of Formula III as measured by HPLC, preferably less than about 0.05% of the compound of Formula III as measured by HPLC, and more preferably is essentially free of compound of Formula III as measured by HPLC.

As per the process reported in Organic Process Research Development 20, 1461-1468, 2016 article, the reaction mass comprising benzyl protected dolutegravir along with open chain impurity in methylene chloride was treated with TBDMS-Cl in presence of imidazole and stirred for 2 hrs; 15% sodium chloride solution was added to the reaction mass, stirred and layers were separated; then the separated organic layer was concentrated under vacuum to get mixture of benzyl protected dolutegravir and silyl derivative of open chain impurity; finally the residue was crystallized from methanol at reflux temperature to remove the formed silyl protected open chain impurity derivative from the reaction mass and to get pure benzyl protected dolutegravir. This process involves the use of TBDMS-Cl for derivatization which is a costly reagent and results in substantial increase of production cost. Further the obtained silyl derivative of open chain impurity is not soluble in water therefore the said impurity can be removed only by additional crystallizations from methanol and this purification is necessary to remove formed silyl protected open chain impurity derivate after basic workup process, which leads to additional process steps and increase the cost of production and not suitable for commercial scale.

In contrast, the present invention purification process of compound of Formula II utilizing inexpensive cyclic anhydrides such as succinic anhydride as a derivatization agent; further the use of cyclic anhydrides as derivatization agent results in the formation of half acid-ester derivative of open chain impurity; and the same will be easily removed by forming water soluble sodium salt during aqueous sodium bicarbonate washings and leaving organic layer containing pure compound of Formula II free of open chain impurity and thereby avoiding additional crystallization to separate pure compound from impurity as like in the prior art. Hence the present invention purification process of compound of Formula II is more advantages over prior art as it encompassing simple workup process, more economic and easy to scale up to commercial level.

Advantages of the Present Invention:
The present invention process is more economical and simple process to remove open chain impurity of Formula III from protected tricyclic carbamoylpyridone derivative of Formula II;
Present invention involves use of inexpensive cyclic anhydrides such as succinic anhydride for derivatization compared to costly reagents of prior art;
Use of cyclic anhydride for derivatization results in the formation half ester-acid of impurity; which is removed by simple aqueous sodium carbonate washing by forming water soluble sodium salt of half ester-acid of impurity; thereby avoiding yield losing crystallization steps of prior art.

EXAMPLES

The following examples are provided by way of illustration only, and are not intended to be limiting of the present invention. Further, the present invention covers all the possible combinations of particular and preferred embodiments indicated herein.

Example 1

Purification of (4R,12aS)—N-(2,4-difluorobenzyl)-7-methoxy-4-methyl-6,8-dioxo-3,4,6,8,12,12a-hexahydro-2H-pyrido[1',2':4,5]pyrazino[2,1-b]oxazine-9-carboxamide (Succinic Anhydride Method)

In 2 lit four necked round bottom flask equipped with mechanical stirrer, thermometer, reflux condenser and an addition funnel, (4R,12aS)—N-(2,4-difluorobenzyl)-7-methoxy-4-methyl-6,8-dioxo-3,4,6,8,12,12a-hexahydro-2H-pyrido[1',2':4,5]pyrazino[2,1-b]oxazine-9-carboxamide (32.5 g, containing 0.7% of 7-(2,4-difluorobenzyl)-9-methoxy-2-[(1R) hydroxy-1-methyl propyl]-1,8-dioxo-1,8-dihydro-2H-pyrido[1,2-a]pyrazine carboxamide), 4-dimethylaminopyridine (7.5 g), succinic anhydride (2.5 g) and methylene chloride (175 ml) was added at 20-25° C. The reaction mass was heated to 35-40° C. and stirred for 4 hrs at the same temperature. Then, the reaction mass was cooled to 25-35° C., 8% aqueous sodium bicarbonate solution (250 ml) was added to it and stirred for 30 mins at 25-35° C. Organic and aqueous layers were separated and organic layer washed with dilute hydrochloric acid, aqueous sodium bicarbonate followed by water. Organic layer was concentrated under vacuum at below 45° C. and diisopropylether (125 ml) was added to the obtained residue and stirred for 2 hrs at 25-35° C. The precipitated solid was filtered, washed with diisopropylether and then dried under vacuum at 50-55° C. for 6 hrs to get pure title compound.

Yield: 31.6 g;

Open chain impurity (7-(2,4-difluorobenzyl)-9-methoxy-2-[(1R)-3-hydroxy-1-methylpropyl]-1,8-dioxo-1,8-dihydro-2H-pyrido[1,2-a]pyrazine-7-carboxamide): Not detected by HPLC Example-2: Purification of (4R,12aS)—N-(2,4-difluorobenzyl)-7-methoxy-4-methyl-6,8-dioxo-3,4,6,8,12,12a-hexahydro-2H-pyrido[1',2':4,5]pyrazino[2,1-b]oxazine-9-carboxamide (Phthalic Anhydride Method)

In 1 lit four necked round bottom flask equipped with mechanical stirrer, thermometer, reflux condenser and an addition funnel, (4R,12aS)—N-(2,4-difluorobenzyl)-7-methoxy-4-methyl-6,8-dioxo-3,4,6,8,12,12a-hexahydro-2H-pyrido[1',2':4,5]pyrazino[2,1-b]oxazine-9-carboxamide (5 g, containing 2% of 7-(2,4-difluorobenzyl)-9-methoxy-2-[(1R)-3-hydroxy-1-methylpropyl]-1,8-dioxo-1,8-dihydro-2H-pyrido[1,2-a]pyrazine-7-carboxamide) and methylene chloride (50 ml) was added at 20-30° C. and stirred for 30 mins. Phthalic anhydride (0.5 g) and 4-dimethylaminopyridine (1.50 g) was added to the reaction mass at 20-30° C. The reaction mass was then heated to 36-40° C. and stirred for 4 hrs at the same temperature. The reaction mass was cooled to 23-27° C. and 8% aqueous sodium bicarbonate solution (50 ml) was added to it and stirred for 30 mins at 25-35° C. Organic and aqueous layers were separated and organic layer washed with dilute hydrochloric acid, aqueous sodium bicarbonate followed by water. Organic layer was concentrated under vacuum at below 45° C., and diisopropylether (50 ml) was added to the obtained residue and stirred for 1 h at 25-35° C. The precipitated solid was filtered, washed with diisopropylether and then dried under vacuum at 50-55° C. to get pure title compound. Yield: 4.5 g;

Open chain impurity (7-(2,4-difluorobenzyl)-9-methoxy-2-[(1R)-3-hydroxy methyl propyl]-1,8-dioxo-1,8-dihydro-2H-pyrido[1,2-a]pyrazine-7-carboxamide): 0.04% by HPLC Example-3: Purification of (2R,5S,13aR)-8-methoxy-7,9-dioxo-N-[(2,4,6-trifluorophenyl)methyl]-2,3,4,5,7,9,13,13a-octahydro-2,5-methano-pyrido[1',2':4,5]pyrazino[2,1-b][1,3]oxazepine-10-carboxamide (Succinic Anhydride Method)

In 2 lit four necked round bottom flask equipped with mechanical stirrer, thermometer, reflux condenser and an addition funnel, (2R,5S,13aR)-8-methoxy-7,9-dioxo-N-[(2,4,6-trifluorophenyl)methyl]-2,3,4,5,7,9,13,13a-octahydro-2,5-methano pyrido[1',2':4,5]pyrazino[2,1-b][1,3]oxazepine-10-carboxamide (204 g, containing about 1.5% of 2-((1R,3S)-3-hydroxy-cyclopentyl)-9-methoxy-1,8-dioxo-1,8-dihydro-2H-pyrido[1,2-a]pyrazine-7-carboxylic acid 2,4,6-trifluoro-benzylamide) and methylene chloride (2 L) was added and stirred for 30 mins at 10-15° C. 4-Dimethylaminopyridine (61.2 g), succinic anhydride (20.4 g) was added to the above reaction mass at 5-15° C. The reaction mass then was heated to 35-40° C. and stirred for 4 hrs. The reaction mass was cooled to 25-35° C., 8% aqueous sodium bicarbonate solution (1 L) was added to it and stirred for 30 mins at 25-35° C. Organic and aqueous layers were separated and organic layer washed with dilute hydrochloric acid, aqueous sodium bicarbonate followed by water. Organic layer was concentrated under vacuum at below 45° C. and diisopropylether (125 ml) was added to the obtained residue and stirred for 2 hrs at 25-35° C. The precipitated solid was filtered, washed with diisopropylether and then dried under vacuum at 50-55° C. for 6 hrs to get pure title compound.

Yield: 194 g;

Open chain impurity 2-((1R,3 S)-3-Hydroxy-cyclopentyl)-9-methoxy-1,8-dioxo-1,8-dihydro-2H-pyrido[1,2-a]pyrazine-7-carboxylic acid 2,4,6-trifluoro-benzylamide: Not detected by HPLC

We claim:

1. A process for purification of protected tricyclic carbamoylpyridone derivatives of Formula II,

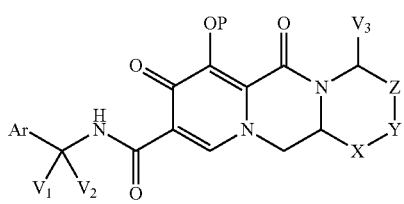

Formula-II or a stereoisomer thereof; wherein,

P is a hydroxy protecting group and is one of a straight or branched chain $C_{1-8}$ alkyl, $C_{1-8}$ halo alkyl, or substituted or unsubstituted silyl or $C_{6-14}$ aryl;

Ar is aryl substituted with one to three halogens;

$V_1$ and $V_2$ are each independently, hydrogen, a $C_{1-6}$ alkyl, or a $C_{1-6}$ haloalkyl; or $V_1$ and $V_2$ together with the carbon atom to which they are attached, form a carbocyclic ring having from 3 to 6 ring atoms or a heterocyclic ring having from 3 to 6 ring atoms, wherein the carbocyclic or a heterocyclic ring is optionally substituted with one or more $R^a$ group;

X is —O—;

Y is —CH($V_5$)—;

Z is a bond, —(CH$_2$—)$_n$ or Y and Z taken together form —(CH$_2$—)$_n$; wherein n is an integer of 0 to 3;

$V_3$ and $V_5$ are each independently, hydrogen, a $C_{1-6}$ alkyl, or a $C_{6-14}$ aryl; or $V_3$ and $V_5$ taken together form a carbocyclic ring containing having from 3 to 6 ring atoms or a heterocyclic ring having from 3 to 6 ring atoms, wherein the carbocyclic or heterocyclic ring is optionally substituted with one or more $R^a$ group, wherein each $R^a$ is, independently, hydrogen, halo, hydroxyl or $C_{1-6}$ alkyl, or wherein two $R^a$ groups together with the carbon atom to which they are attached to form =O;

the process comprising:

a) reacting a compound of Formula II comprising a compound of Formula III,

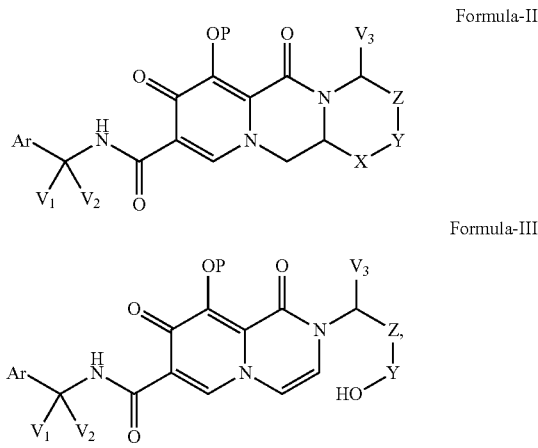

wherein P, Ar, $V_1$, $V_2$, $V_3$, X, Y and Z are as defined above, with a $C_4$-$C_{20}$ substituted or unsubstituted cyclic anhydride in a suitable solvent;

b) treating the reaction mass with an aqueous basic solution; and c) isolating the compound of Formula II substantially free of the compound of Formula III.

2. The process as claimed in claim 1, wherein P is methyl, Ar is 2,4-difluorophenyl, $V_1$ and $V_2$ are independently hydrogen, $V_3$ is methyl, X is —O—, Y and Z are independently CH$_2$.

3. The process as claimed in claim 1, wherein P is methyl, Ar is 2,4,6-trifluorophenyl, $V_1$ and $V_2$ are hydrogen, $V_3$ is hydrogen, X is —O—, Y is —CH($V_5$)—, Z is —CH$_2$—, and $V_3$ and $V_5$ together form a cyclopentane ring.

4. The process as claimed in claim 1, wherein the $C_4$-$C_{20}$ substituted or unsubstituted cyclic anhydride is selected from one of succinic anhydride, phthalic anhydride, glutaric anhydride, or maleic anhydride.

5. The process as claimed in claim 1, wherein the suitable solvent is selected from the group consisting of halogenated hydrocarbons, hydrocarbons, ketones, esters, ethers, nitriles, amides, sulfoxides, and mixtures thereof.

6. The process as claimed in claim 4, wherein the cyclic anhydride is succinic anhydride or phthalic anhydride.

7. The process as claimed in claim 5, wherein the solvent is one of or a mixture of more than one of methylene chloride, chloroform, toluene, xylene, heptane, hexane, acetone, methyl ethyl ketone, methyl isobutyl ketone, ethyl acetate, propyl acetate, isopropyl acetate, butyl acetate, tetrahydrofuran, dimethyl ether, isopropyl ether, methyl tertiary butyl ether, 1,4-dioxane, acetonitrile, N,N-dimethylformamide, N,N-dimethylacetamide, and dimethylsulfoxide.

8. The process as claimed in claim 1, wherein the step a) reaction is carried out in the presence of a base selected from the group consisting of triethylamine, isopropyl ethylamine, diisopropylamine, diisopropylethylamine, N-methylmorpholine, 4-dimethylamino pyridine, piperidine, pyridine, and mixtures thereof.

9. The process as claimed in claim 8, wherein the base is 4-dimethylaminopyridine.

10. The process as claimed in claim 1, wherein the step b) further comprises separating the organic layer and aqueous layer from the step b) solution and concentrating the organic layer.

11. The process as claimed in claim 1, wherein the step a) and the step b) are each carried out at a temperature of from 10° C. to reflux temperature.

12. The process as claimed in claim 1, wherein the isolated compound of Formula II obtained in step c) is characterized as having less than 0.1% of the compound of Formula III as measured by HPLC.

13. A process for purification of a methoxy derivative compound of Formula IIA comprising:
a) reacting a compound of Formula IIA comprising a compound of Formula IIIA

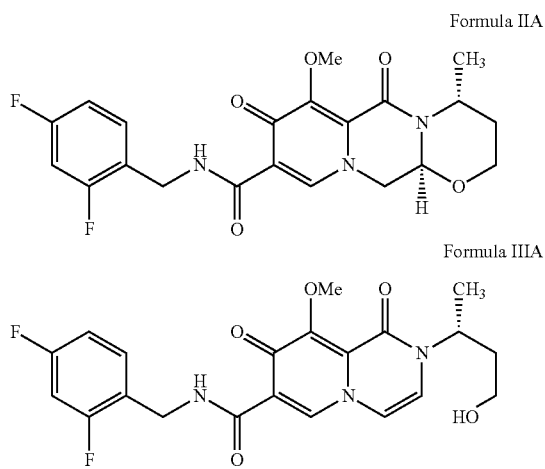

Formula IIA

Formula IIIA with a $C_4$-$C_{20}$ substituted or unsubstituted cyclic anhydride in a suitable solvent in the presence of a base;
b) treating the reaction mass obtained in step a) with an aqueous basic solution;
c) separating the organic layer and aqueous layer;
d) concentrating the organic layer, and
e) isolating the compound of Formula IIA substantially free of the compound of Formula IIIA.

14. The process as claimed in claim 13, wherein in step a) the base is selected from the group consisting of triethylamine, isopropyl ethylamine, diisopropylamine, diisopropylethylamine, N-methylmorpholine, 4-dimethylaminopyridine, piperidine, pyridine, and mixtures thereof.

15. The process as claimed in claim 13, wherein the unsubstituted cyclic anhydride is one of succinic anhydride or phthalic anhydride; the base is 4-dimethylaminopyridine;

the solvent is methylene chloride; and the aqueous basic solution is aqueous sodium bicarbonate.

16. A process for preparation of tricyclic carbamoylpyridone derivatives of Formula I,

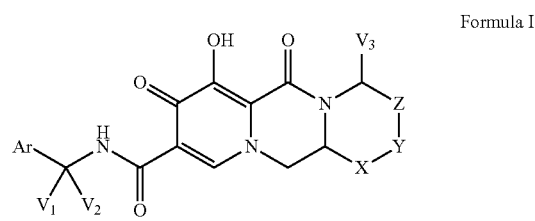

Formula I or a stereoisomer or pharmaceutically acceptable salt thereof, wherein Ar is aryl substituted with one to three halogens;
$V_1$ and $V_2$ are each independently, hydrogen, $C_{1-6}$ alkyl, or $C_{1-6}$ haloalkyl; or $V_1$ and $V_2$ together with the carbon atom to which they are attached, form a carbocyclic ring having from 3 to 6 ring atoms or a heterocyclic ring having from 3 to 6 ring atoms, wherein the carbocyclic or a heterocyclic ring is optionally substituted with one or more $R^a$ group;
X is —O—,
Y is —CH($V_5$)—;
Z is a bond, (—$CH_2$—)$_n$ or Y and Z taken together form (—$CH_2$—)$_n$; wherein n is an integer of 0 to 3;
$V_3$ and $V_5$ are each independently, hydrogen or $C_{1-6}$ alkyl, $C_{6-14}$ aryl or $V_3$ and $V_5$ taken together form a carbocyclic ring containing having from 3 to 6 ring atoms or a heterocyclic ring having from 3 to 6 ring atoms, wherein the carbocyclic or heterocyclic ring is optionally substituted with one or more $R^a$ group; wherein each $R^a$ is, independently, hydrogen, halo, hydroxyl or $C_{1-6}$ alkyl, or wherein two $R^a$ groups together with the carbon atom to which they are attached to form =O;
the process comprising:
i) preparing the compound of Formula II substantially free of the compound of Formula III according to the process as claimed in claim 1, and
ii) converting the compound of Formula II into the compound of Formula I by deprotecting the hydroxy group.

17. The process as claimed in claim 16, wherein the compound of Formula I is one of the compound of Formula IA, the compound of Formula IB, or the compound of Formula IC;

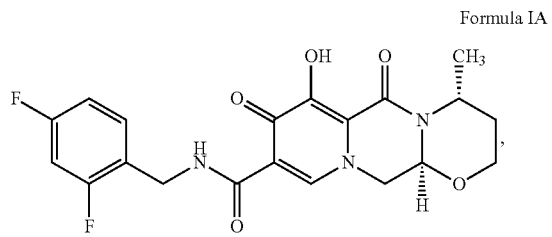

Formula IA

-continued
Formula IB
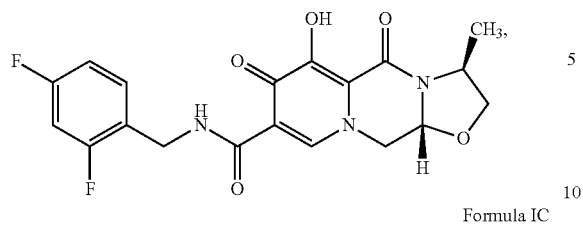
Formula IC
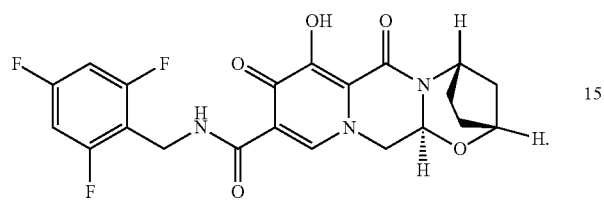
* * * * *